Figure 1:
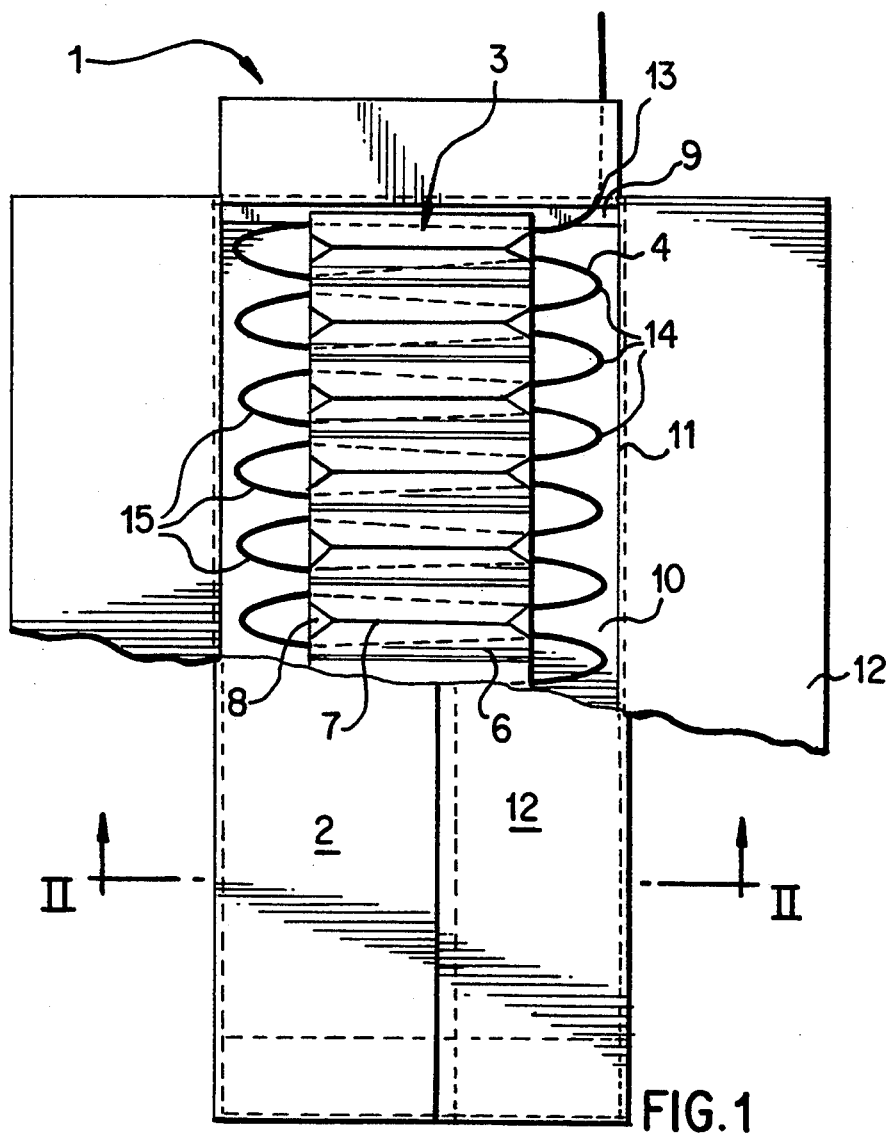

United States Patent [19]
Schönke

[11] Patent Number: 5,413,214
[45] Date of Patent: May 9, 1995

[54] SUTURE HOLDER

[75] Inventor: Ingoberth Schönke, Henstedt-Ulz-burg, Germany

[73] Assignee: Deknatel Medizinische Produkte GmbH, Germany

[21] Appl. No.: 66,026

[22] PCT Filed: Sep. 18, 1992

[86] PCT No.: PCT/DE92/00806

§ 371 Date: Sep. 20, 1993

§ 102(e) Date: Sep. 20, 1993

[87] PCT Pub. No.: WO93/05714

PCT Pub. Date: Apr. 1, 1993

[30] Foreign Application Priority Data

Sep. 20, 1991 [DE] Germany .................. 41 31 269.4

[51] Int. Cl.⁶ .................. A61B 17/06; B65D 65/10
[52] U.S. Cl. .................. 206/63.3; 206/388; 206/478
[58] Field of Search .................. 206/63.3, 227, 382, 206/388, 478, 479, 553

[56] References Cited

U.S. PATENT DOCUMENTS 2,587,559  2/1952  Wetherbee .................. 206/553 X
3,341,066  9/1967  Bower .
4,014,434  3/1977  Thyen .
4,699,271 10/1987  Lincoln et al. .................. 206/63.3
5,024,324  6/1991  Whittaker .................. 206/388 X

FOREIGN PATENT DOCUMENTS 531113      8/1954   Belgium .................. 206/388
0168172     1/1986   European Pat. Off. .
0521170B1   4/1994   European Pat. Off. .
908792     11/1963   France .
2374016     7/1978   France .
1290296     3/1969   Germany .
1935364    11/1970   Germany .
3027836     3/1982   Germany .
335442     12/1958   Switzerland .................. 206/479
1590967     6/1981   United Kingdom .

Primary Examiner—Bryon P. Gehman
Attorney, Agent, or Firm—Pennie & Edmonds

[57] ABSTRACT

The suture holder is provided for a plurality of individually removable strands, in particular surgical suture material. The sutures are guided, as a bundle of strands, in parallel paths through these surrounding hollow tubular members, the paths running through the hollow members in pairs and the pairs of paths being separated from one another by the hollow members. All sutures are guided through the holder in one bundle of strands, with multiple changes of direction, in the same paths. In addition, in the reversing region of adjacent hollow members they are supported by a wall arranged transverse to the parallel paths.

17 Claims, 2 Drawing Sheets

SUTURE HOLDER

The invention concerns a suture holder for a plurality of individually removable strands, in particular surgical suture materials, wherein the strands are carried in parallel paths through surrounding hollow tubular members, the paths running through the hollow members in pairs and the path pairs being separated from one another by the hollow members.

Such a suture holder is disclosed in, for example, DE 30 27 836 A1. In this suture holder hollow rectangular members, which are arranged parallel to one another and in which the strands are guided, are formed. To prevent entanglement of the strands, only one strand is arranged in each hollow member, specifically, running through the hollow member in two parallel paths.

Although such completely separate guidance of the individual strands ensures relatively good individual removal without interfering with the remaining strands, this known suture holder is suitable only for sutures which are short in length, since otherwise the length and hence the size of the holder increases so that handling in the operating room is severely restricted or made impossible because of the great amount of space required.

In the past, therefore, it has always been sought to design such suture holders, suture packs, dispenser packs or the like for a plurality of individually removable sutures so that the size of the assembly is as independent as possible of suture length, suture thickness and number of sutures. Numerous accomplishments are known in which the sutures are laid inside a container in loops Common to all of these accomplishments is the problem that reliable removal of an individual strand cannot be sufficiently guaranteed. Problems recur repeatedly, particularly with very long and relatively thin sutures, so that individual packs are often selected for these sutures.

Such an individual suture pack is disclosed, for example, in EP 0,168,172 B1. The suture holder described there guides the suture, laid double and winding sinuously in parallel paths, through the suture holder. A reversal of direction at the end of the holder causes both ends of the strand to emerge at the entrance of the holder. However, this suture holder is provided and is suitable for accommodating only a single suture.

Starting from the state of the art mentioned at the beginning, the object of the invention is to design a generic suture holder for a plurality of sutures so that even relatively long and/or thin sutures can be stored compactly and removed individually with the necessary dependability without risk of entanglement.

According to the invention, this object is accomplished, in a suture holder for a plurality of individually removable strands, by guiding the strands in parallel paths through surrounding hollow tubular members, the path running through the hollow members in pairs and the pairs of paths being separated from one another by the hollow members, wherein that the sutures are guided as a bundle of strands winding sinuously through the suture holder in the same paths with multiple changes of direction, and wherein the strands are supported in the reversing region of adjacent hollow members by a wall arranged transverse to the parallel paths.

The suture holder according to the invention may be designed as one piece or as a plurality of pieces, and parts of the packaging may alternatively belong to the suture holder within the meaning of the invention.

The suture holder according to the invention permits compact and at the same time more accessible arrangement of a plurality of sutures of virtually unlimited length as well as of small thickness. In particular, with the suture holder according to the invention even sutures which hitherto have always had to be handled in individual holders or individual packs may alternatively be arranged compactly in multiples in a minimum of space. At the same time, the suture holder according to the invention does not require the sutures to be laid in any particular order or one after the other; they may be arranged as desired and, within limits, even be twisted together in the suture holder, without this hindering removability of an individual strand without interference with the remaining sutures located in the holder. This results in special advantages in loading of the suture holder according to the invention, since suture guidance inside the loading machine may be effected unsorted and hence in a very simple way.

Support of the strands in the reversing region by a wall arranged transverse to the parallel paths is required to ensure individual removability without interference with the other strands remaining in the holder. A wall may be provided in each instance at each reversing region of adjacent hollow members, but the design is especially advantageous and structurally simple when a common continuous wall is provided at the side of the hollow members at which the strands are guided from one such member into the adjacent member.

The suture holder is preferably designed so that the reversing regions are arranged outside the hollow members. In this way, for one thing the suture holder can be produced with an economical use of material and, for another, suture thickness and suture count are clearly visible, especially in transparent packagings. Lastly, this arrangement likewise considerably simplifies loading of the suture holder with sutures.

The hollow tubular members are advantageously arranged side by side, specifically preferably in one plane, and joined together laterally. Thus the hollow members may be designed inexpensively as one piece, for example as an injection molding.

It has been found, surprisingly, that the suture holder according to the invention is advantageously designed so that the respective length of the parallel paths is shorter than the width of the hollow members arranged side by side, for the number of reversals and hence of parallel paths plays practically no role in the suture holder according to the invention; in particular, an increase in this number of paths in no way interferes with individual removability of the strands, at least so far as sutures of commercially available length are concerned. Owing to this, the outer dimensions of the suture holder may be sized virtually independently of suture length, which is of great advantage especially with regard to storage and packaging.

It is convenient for the hollow tubular members in each instance to have, preferably on their upper side, a continuous closable longitudinal slot for the passage of an instrument for the insertion of sutures, which is advantageously provided at both its ends with a feed opening for introduction of the instrument. This makes it possible to insert an instrument drawing the sutures for guidance into the suture holder, which, for example, is able to pass through the individual hollow members from above like a needle, without having to put up with the disadvantage of the hollow members not being designed essentially closed over their entire periphery, this being disclosed to be disadvantageous in, for example, EP 0,168,172 B1. Otherwise, because of the numerous sutures lying within the tubular hollow members, individual sutures might under certain circumstances be forced out, which should be avoided.

To combine the hollow members, closed in peripheral direction, on the one hand, and the longitudinal slot, highly advantageous for loading, on the other, in a structurally simple fashion, the invention provides that each tubular hollow member is designed spring-elastically in peripheral direction, specifically, so that its longitudinal slot is automatically held in closed position by mutual contact or overlapping of its ends limiting the slot laterally.

The inner contour of the tubular hollow member of the suture holder according to the invention is in principle freely selectable, but if possible the inner contour should be designed rounded. The inner contour is preferably round.

The suture holder according to the invention may be designed in one piece when the wall supporting the sutures in the reversing region is formed on the hollow tubular members. Such a shaped part may be produced as, for example, an injection molding.

This wall (or these walls) required for individual removal of the sutures may alternatively be formed by a part of the wrapper, since such suture holders are customarily arranged in a wrapper anyway. Then such a wrapper advantageously consists of a folding box or at least a closable shaped part. A shell of synthetic material closable by means of film may, for example, be used as a shaped part. However, in the case of a wrapper of shaped parts a two-shell packaging made of two formed parts joined together will preferably be used for accommodating the suture holder. Then this wrapper forms a functional unit with the holder itself lying inside and thus is part of the suture holder.

The invention is explained in detail below by examples illustrated in the drawings, wherein FIG. 1 shows a top view of a suture holder with wrapper with packaging partially open, FIG. 2, a section along the sectional line II—II in FIG. 1, FIG. 3, another embodiment of a suture holder with wrapper in a representation according to FIG. 2, FIG. 4, a top view of the holder of FIG. 1 without sutures, FIG. 5, a side view in the direction of the arrow V in FIG. 4 and FIG. 6, a side view in a representation according to FIG. 5 of the suture holder of FIG. 3.

The storage container and dispenser 1 for surgical suture material illustrated in FIG. 1 consists essentially of a wrapper 2 and a suture holder 3 arranged therein, wherein a plurality of strands 4 of surgical suture material are arranged lying side by side -in sinuous parallel paths 5.

The suture holder 3 itself consists of a plurality of tubular sections 6, arranged side by side in one plane, which in each instance have a longitudinal slot 7 running over the entire length at their upper side and which are joined together side by side. The longitudinal slots 7 are provided at either end with a wedge-shaped feed opening at the slot. These serve for the passage of instruments which draw the suture loops through the tubular sections 6 for the purpose of loading. The tubular sections 6 consist of elastic synthetic material, so that the longitudinal slots 7 are automatically closed by virtue of the spring force of the tubes. In this connection, the tubular sections 6 may be designed either so that they are contiguous or alternatively overlap the tubular sides limiting the longitudinal slot 7. In the case of thin material, overlapping will be preferable, while with great wall thicknesses abutment of the sides of the tube will be advantageous. In the tubular sections 6 illustrated in the figures, the sides of the tube abut one another.

At its end sides in top view the suture holder 3, formed of tubular sections 6, has approximately rectangular shapes 9, which serve as spacers. These spacers 9, firmly connected with the end-side tubular sections 6, project beyond the tubular sections 6 in length, so that they center the holder 3 centrically within the wrapper 2. The wrapper 2, represented by means of FIGS. 1 and 2, is a rectangular folding box of cardboard or other suitable material, consisting of a floor 10, four side walls 11 and four flaps 12, articulated at the side walls 11 and forming the cover, which, as shown in FIG. 2, can be folded overlapping for complete encasement of the suture holder 3 with the sutures 4 located therein. An opening 13, through which the ends of the suture 4 are carried out of the wrapper 2, is provided in one of the narrow side walls 11.

Figure 2:
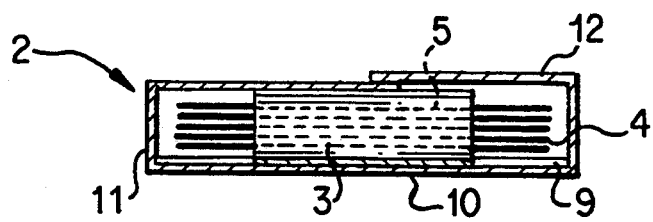

The sutures 4, which are schematically represented lying over one another in FIG. 2, lie side by side in any desired arrangement and are jointly guided winding sinuously in the paths 5 running through the entire container 1 and emerging from the opening 13. In this connection, the sutures 4 are guided so that two paths 5 run through each tubular section 6, all reversing regions of the sutures lying outside the tubular sections 6 and thus the suture holder 3. In this way each strand is guided through each tubular section 6 in two parallel lengths. Reversing regions 14, in which the sutures 4 coming from a tubular section are guided into the adjacent tubular section 6 with a 360-degree change of direction, are therefore produced on one side of the tubular sections 6. By contrast, reversing regions 15, in which the sutures 4 are likewise reversed 360 degrees, but back into the tubular section 6 from which they come, are produced on the other side. The sutures 4 are supported by a wall of the suture holder or alternatively the wrapper, at least in the region of the reversing regions 14 first mentioned. In the examples illustrated, support is provided by a wall of the wrapper, in FIG. 1, for example, by one of the side walls 11. In FIG. 4 a broken line 16 indicates how such a supporting wall for the reversing regions 14 might be designed as one piece with the suture holder 3. These walls 11, supporting the reversing regions 14 and 15, ensure that upon removal of an individual strand the other sutures 4 remain unchanged in their position in the suture holder.

Figure 3:
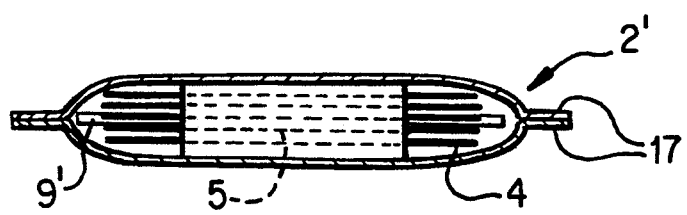
Figure 4:
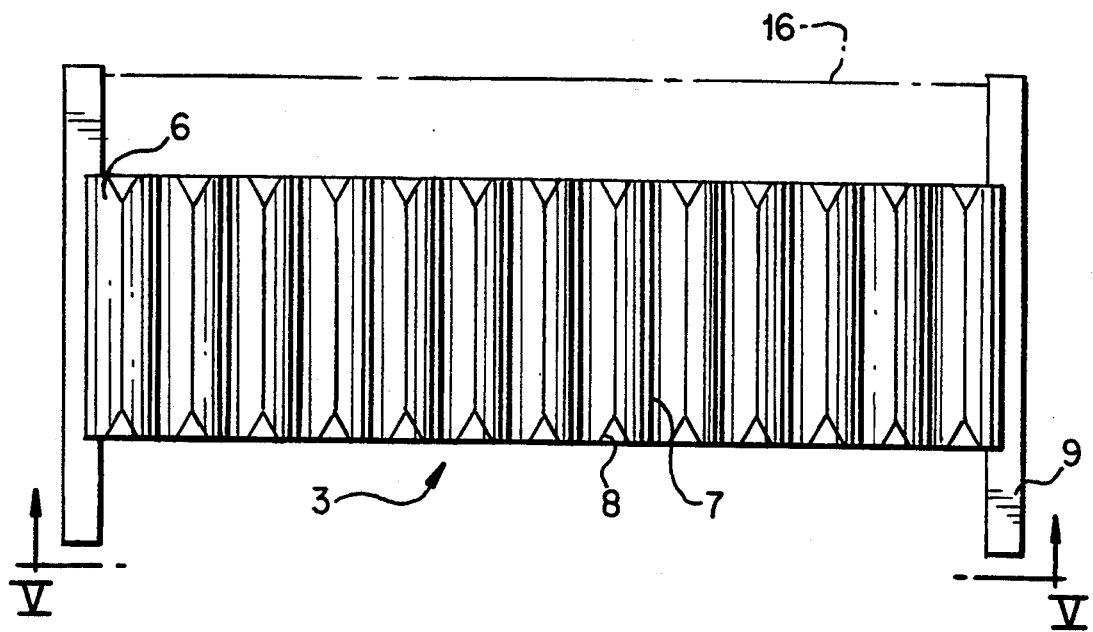

FIG. 3 shows a wrapper 2' which consists of synthetic material and is formed of two half shells 17. Since the half shells 17 are designed tub-shaped, the spacer 9' must be arranged in the mid-plane of the tubular sections 6, while in the embodiment of FIGS. 1 and 2 it may lie in a plane parallel thereto.

Figure 5:
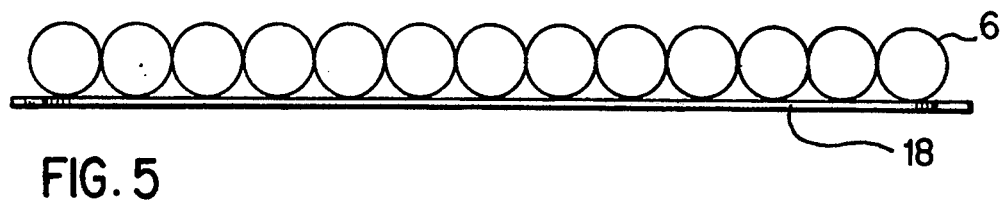
Figure 6:
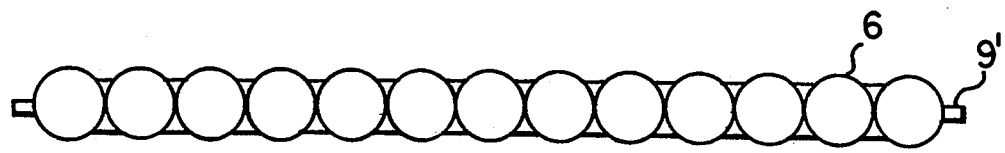

FIGS. 5 and 6 illustrate various types of the connection of tubular sections 6 with one another. In the embodiment of FIG. 5 the tubular sections 6, resting against one another, are joined together by a continuous lower bottom plate 18. In the embodiment of FIG. 6, on the other hand, the tubular sections 6 are part of a molded member and are directly joined together laterally. The spacers 9' are likewise formed on the tubular sections 6 laterally.

The suture holder described above and/or the wrapper may alternatively, for example, be lengthened on one side to simultaneously form a needle holder when the suture holder is designed to be used for sutures with swaged needles. Although only four or five sutures 4 are shown schematically in the figures, initial tests have already demonstrated that, without an additional bundle of sutures, from ten to thirty individual strands in lengths of, for example, one meter can be accommodated by the suture holder described above.

We claim:

1. Suture holder for a plurality of individually removable strands, comprising:
    a plurality of hollow tubular members each having a first open end and a second open end opposed to said first open end;
    plurality of individually removable strands disposed as a bundle of strands, wherein each strand winds sinuously through each of said hollow tubular members in generally parallel paths through said hollow tubular members and the paths being separated from one another by said hollow tubular members with multiple changes of direction adjacent said first open ends and said second open ends of said hollow tubular members such that each strand reverses direction adjacent said first and said second open ends of said tubular members; and
    end wall means disposed adjacent and generally opposite each of said first and said second open ends of said hollow tubular members for supporting reversed portions of said strands such that said strands can be stored compactly and removed individually so as to avoid entanglement, wherein the position of said end wall means remain generally unchanged relative to said reversed portions of the strands remaining in said holder during removal of individual strands.

2. Suture holder according to claim 1, wherein said end wall means comprises a common continuous end wall adjacent and generally opposite said first open ends of said hollow members and a common continuous end wall adjacent and generally opposite said second open ends of said hollow members.

3. Suture holder according to claim 1, wherein said end wall means is configured to permit said strands to reverse direction outside of said hollow tubular members.

4. Suture holder according to claim 1, wherein said hollow tubular members are joined together side by side.

5. Suture holder according to claim 4, wherein the respective length of the parallel paths is shorter than the width of said joined hollow tubular members arranged side by side.

6. Suture holder according to claim 1, wherein each of said hollow tubular members has a generally rounded inner contour.

7. Suture holder according to claim 1, wherein said hollow tubular members are integrally injection molded.

8. Suture holder according to claim 1, wherein said end wall means for supporting said reversed portions of said strands further includes at least one wall arranged contiguous with said hollow tubular members.

9. Suture holder according to claim 1, further comprising means for containing said hollow tubular members, wherein at least a part of said containing means forms said end wall means which support said strands where the strands reverse direction.

10. Suture holder according to claim 9, wherein said containing means is a wrapper formed by a folding box.

11. Suture holder according to claim 9, wherein said containing means is a wrapper made of at least one closable formed part.

12. Suture holder according to claim 1, wherein said wall means is generally transverse to the generally parallel paths of said strands.

13. Suture holder for a plurality of individually removable surgical suture strands, comprising:
    a plurality of hollow tubular members each having a first end and a second end, wherein said hollow tubular members permit said strands to be disposed as a bundle of strands winding sinuously through said hollow tubular members in generally parallel paths through said hollow tubular members and the paths being separated from one another by said hollow tubular members with multiple changes of direction adjacent said first ends and said second ends of said hollow tubular members such that said strands reverse direction adjacent said first and said second ends of said tubular members; and
    wall means disposed adjacent said first ends and said second ends of said hollow tubular members for supporting reversed portions of said strands such that said strands can be stored compactly and removed individually so as to avoid entanglement,
    wherein each of said hollow tubular members has a continuous closable longitudinal slot for passage of an instrument for inserting said strands, wherein each slot is provided at both its ends with a feed opening.

14. Suture holder according to claim 13, wherein each of said tubular hollow members is elastic and biased to have its longitudinal slot automatically closed by mutual contact or overlapping of its ends bounding the slot laterally.

15. Suture holding apparatus for holding a plurality of individually removable strands comprising:
    a plurality of hollow tubular members each having a first end and a second end opposed to said first end;
    a plurality of individually removable strands disposed as a bundle of strands, each strand winding sinuously through each of said hollow tubular members in generally parallel paths through said hollow tubular members and the paths being separated from one another by said hollow tubular members with multiple changes of direction adjacent said first ends and said second ends of said hollow tubular members such that said strands reverse direction adjacent said first and said second ends of said tubular members; and
    an end wall disposed adjacent and generally opposite each of said first and second open ends of said tubular members for supporting reversed portions of said strands such that said strands can be stored compactly and removed individually without interference with other strands remaining in said hollow tubular members so as to avoid entanglement, wherein the position of both end walls remain generally unchanged relative to said reversed portions of the strands remaining in said holder during removal of individual strands.

16. Suture holding apparatus according to claim 15, wherein said strands reverse direction outside of said hollow tubular members.

17. Suture holding apparatus according to claim 15, wherein the respective length of the parallel paths is shorter than the length of said hollow members.

* * * * *